United States Patent [19]

Carpentieri

[11] Patent Number: 5,707,391

[45] Date of Patent: Jan. 13, 1998

[54] APPARATUS AND METHOD FOR ATTACHING SURGICAL NEEDLE SUTURE COMPONENTS

[75] Inventor: Richard P. Carpentieri, Plantsville, Conn.

[73] Assignee: United States Surgical Corporation, Norwalk, Conn.

[21] Appl. No.: 474,346

[22] Filed: Jun. 7, 1995

[51] Int. Cl.$^6$ ...................................................... A61B 17/00
[52] U.S. Cl. .............. 606/223; 606/226; 72/469; 29/515; 29/748; 29/753
[58] Field of Search .................. 606/222–227; 163/5; 289/16; 206/380; 112/222, 80.06, 80.17; 72/469, 470; 29/515–517, 748, 753

[56] References Cited

U.S. PATENT DOCUMENTS

| | | |
|---|---|---|
| Re. 27,735 | 8/1973 | Shave et al. . |
| Re. 31,084 | 11/1982 | Birks . |
| 1,558,037 | 10/1925 | Morton . |
| 1,578,543 | 3/1926 | Montgomery . |
| 2,067,568 | 1/1937 | Grunthal . |
| 2,205,893 | 6/1940 | Unger . |
| 2,411,079 | 11/1946 | Baule . |
| 2,620,028 | 12/1952 | Kohut . |
| 2,958,929 | 11/1960 | Vineberg et al. . |
| 2,983,898 | 5/1961 | Kalmar et al. . |
| 3,055,412 | 9/1962 | Dibner . |
| 3,611,551 | 10/1971 | Shave et al. . |
| 3,643,327 | 2/1972 | Jackson . |
| 3,771,343 | 11/1973 | Dawson . |
| 3,890,975 | 6/1975 | McGregor . |
| 3,910,282 | 10/1975 | Messer et al. . |
| 3,963,031 | 6/1976 | Hunter . |
| 3,972,219 | 8/1976 | Riehl . |
| 3,980,177 | 9/1976 | McGregor . |
| 4,027,519 | 6/1977 | Backle . |
| 4,047,420 | 9/1977 | Edwards . |
| 4,054,144 | 10/1977 | Hoffman et al. . |
| 4,060,885 | 12/1977 | Hoffman et al. . |
| 4,067,224 | 1/1978 | Birks . |
| 4,072,041 | 2/1978 | Hoffman et al. . |
| 4,124,027 | 11/1978 | Boss . |
| 4,192,171 | 3/1980 | Hamilton . |
| 4,292,833 | 10/1981 | Lapp . |
| 4,361,948 | 12/1982 | Omata . |
| 4,498,222 | 2/1985 | Ono et al. . |
| 4,567,650 | 2/1986 | Balyasny et al. . |

(List continued on next page.)

FOREIGN PATENT DOCUMENTS

| | | |
|---|---|---|
| 0249504 | 12/1987 | European Pat. Off. . |
| 1526222 | 9/1978 | United Kingdom . |

*Primary Examiner*—Jeffrey A. Schmidt

[57] ABSTRACT

Apparatus for attaching a surgical needle having an end portion with an elongated aperture defined therein and a suture having a generally elongated end portion to be positioned in the elongated aperture of the needle, includes a pair of dies, each die defining a longitudinal axis and having an inner die surface. The inner die surface includes at least two raised swaging portions extending generally along the longitudinal axis of the die and a generally recessed portion defined between adjacent swaging portions and extending substantially along the lengths thereof. The swaging portions each have an engaging surface defining a plane angularly oriented relative to a longitudinal bisecting plane of the dies. The recessed portion defines a relief zone such that when the end portion of the suture is positioned within the aperture of the needle end and the dies are positioned about the end portion of the needle with the at least two swaging portions of each die generally facing the outer surface of the needle, applying inward crimping force to the dies causes the engaging surfaces of the dies to produce inward crimping forces on opposed sides of the needle end portion to cause a reduction of the dimension of the elongated aperture of the needle to thereby attach the needle to the suture, wherein the recessed portion defined between the adjacent swaging portions receive and collect deformed material from the needle. A method for attaching a surgical suture to a needle with the dies is also disclosed.

27 Claims, 6 Drawing Sheets

U.S. PATENT DOCUMENTS

| | | |
|---|---|---|
| 4,672,734 | 6/1987 | Kawada . |
| 4,719,789 | 1/1988 | Wiebe et al. . |
| 4,722,384 | 2/1988 | Matsutani . |
| 4,799,311 | 1/1989 | Matsutani . |
| 4,805,292 | 2/1989 | Noguchi . |
| 4,890,614 | 1/1990 | Kawada . |
| 4,910,857 | 3/1990 | Tanaka et al. . |
| 4,922,904 | 5/1990 | Uetake et al. . |
| 5,001,323 | 3/1991 | Matsutani et al. . |
| 5,012,066 | 4/1991 | Matsutani et al. . |
| 5,046,350 | 9/1991 | Proto et al. . |
| 5,084,963 | 2/1992 | Murray . |
| 5,099,676 | 3/1992 | Proto et al. . |
| 5,131,131 | 7/1992 | Proto et al. . |
| 5,168,619 | 12/1992 | Proto et al. . |
| 5,201,760 | 4/1993 | West . |
| 5,207,701 | 5/1993 | West . |
| 5,224,955 | 7/1993 | West . |
| 5,230,352 | 7/1993 | Putnam et al. . |
| 5,383,902 | 1/1995 | Carpentiere et al. .................. 606/222 |

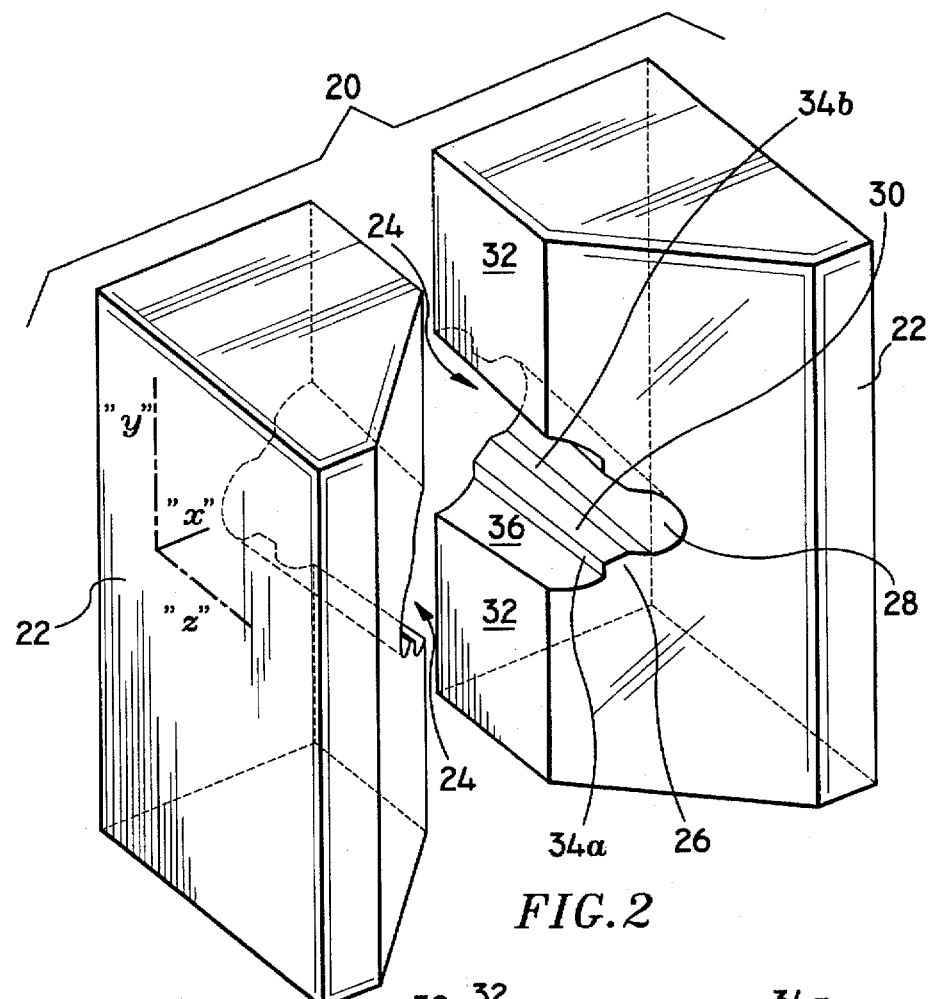
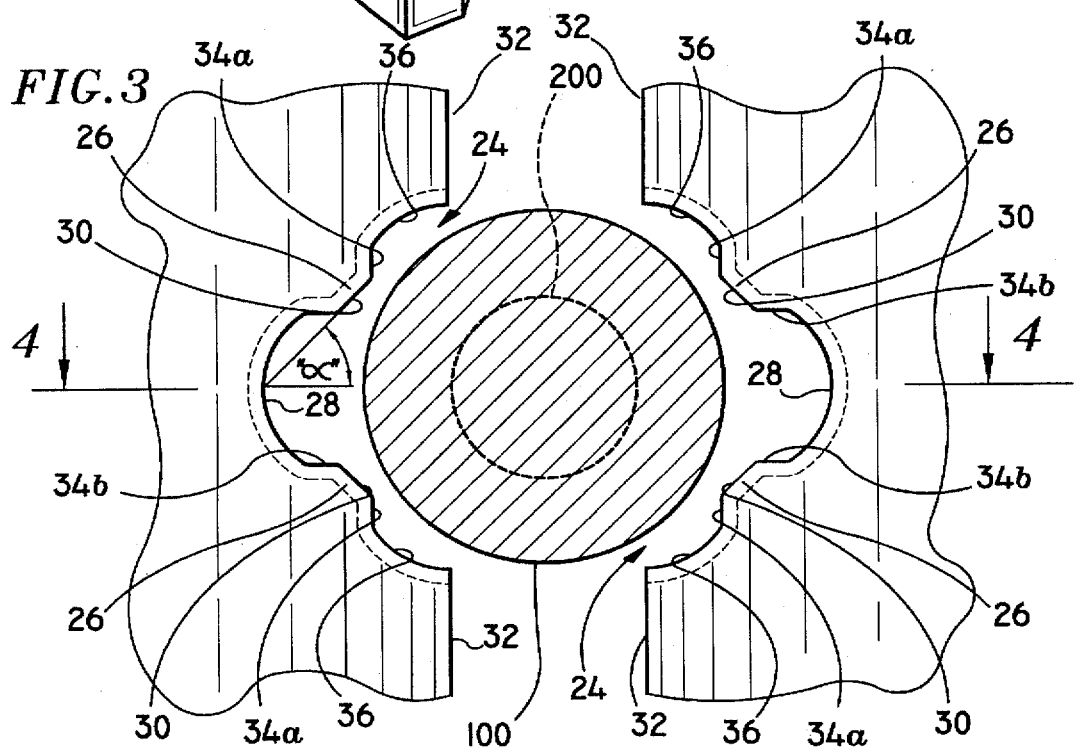

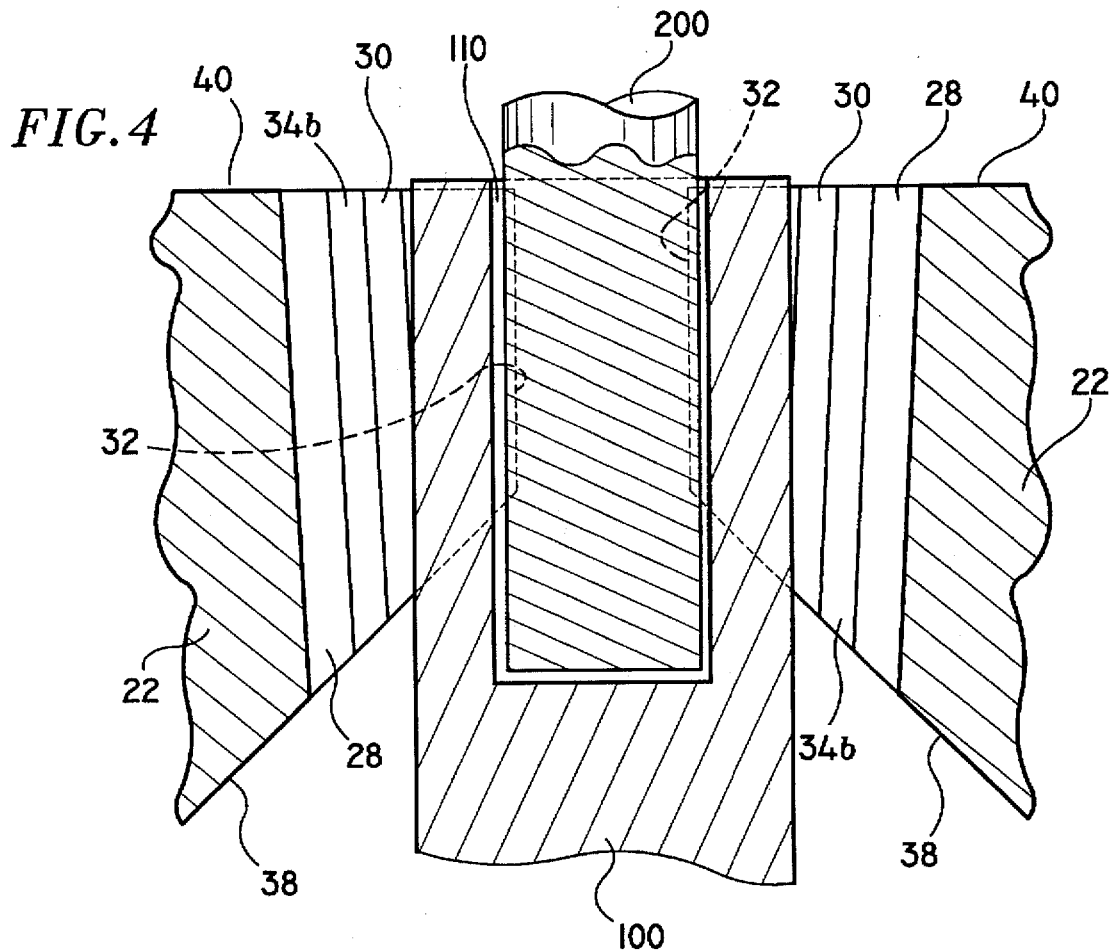
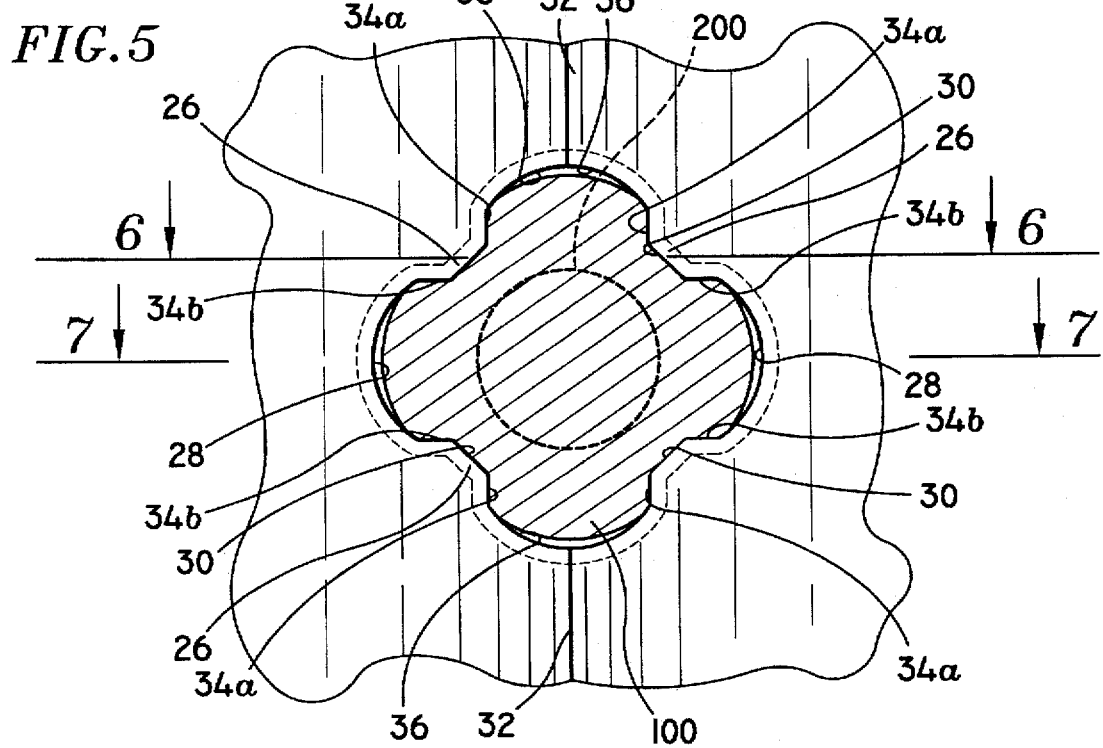

APPARATUS AND METHOD FOR ATTACHING SURGICAL NEEDLE SUTURE COMPONENTS

BACKGROUND

1. Technical Field

The present disclosure relates to the attachment of surgical sutures to surgical needles. In particular, the disclosure relates to a method and apparatus for the attachment of surgical needles to surgical sutures to provide a combined surgical needle-suture device.

2. Background of Related Art

For many years, surgeons have employed needle-suture combinations in which a suture or ligature is attached to the shank end of a needle. Such needle-suture combinations are provided for a wide variety of monofilament and braided suture materials, both absorbable and non-absorbable, e.g., catgut, silk, nylon, polyester, polypropylene, linen, cotton, and absorbable synthetic materials such as polymers and copolymers of glycolic and lactic acids.

Needle-suture combinations fall into two general classes: standard needle attachment and removable or detachable needle attachment. In the case of standard needle attachment, the suture is securely attached to the needle and is not intended to be separable therefrom, except by cutting or severing the suture. Removable needle attachment, by contrast, is such that the needle is separable from the suture in response to a force exerted by the surgeon. Minimum acceptable forces required to separate a needle from a suture for various suture sizes are set forth in the United States Pharmacopeia (USP XXII 1990).

One typical method for securing a suture to a needle involves providing a cylindrical recess in the shank end of a needle and securing a suture therein. For example, U.S. Pat. No. 1,558,037 teaches the addition of a cement material to such a substantially cylindrical recess to secure the suture therein. Additional methods for bonding a suture within a needle bore are described in U.S. Pat. Nos. 2,928,395 (adhesives) and 3,394,704 (bonding agents). Alternatively, a suture may be secured within an axial bore in a needle by swaging the needle in the region of the recess, see, e.g., U.S. Pat. No. 1,250,114. Additional prior art methods for securing a suture within a needle bore include expansion of a catgut suture through the application of heat (U.S. Pat. No. 1,665,216), inclusion of protruding teeth within the axial bore to grasp an inserted suture (U.S. Pat. No. 1,678,361) and knotting the end of the suture to be inserted within the bore to secure the suture therein (U.S. Pat. No. 1,757,129).

Methods for detachably securing a suture to a needle are also well known. For example, U.S. Pat. Nos. 3,890,975 and 3,980,177 teach swaging a suture within a needle bore such that the suture has a pull-out value of 3 to 26 ounces. Alternative detachable attachment methods include providing a weakened suture segment (U.S. Pat. No. 3,949,756), lubricant tipping the end of a suture to be inserted in the axial bore of a needle (U.S. Pat. No. 3,963,031) and pretensioning a suture that is swaged within an axial needle bore (U.S. Pat. No. 3,875,946). See also, U.S. Pat. Nos. 3,799,169; 3,880,167; 3,924,630; 3,926,194; 3,943,933; 3,981,307; 4,124,027; and 4,127,133.

A prevailing method for forming either a detachable or non-detachable needle-suture device or combination incorporates a swage or crimp attachment. Typically, a swage or crimp attachment can be accomplished by use of a "drilled end needle", i.e., one in which a concentric aperture is formed in the end of the needle in which is the suture is placed and the needle is crimped around the suture. Examples of such attachment methods are described in the aforementioned U.S. Pat. Nos. 3,890,975 and 3,980,177. Swaging dies for achieving removable needle attachment are disclosed in U.S. Pat. Nos. 4,060,885 and 4,072,041.

The swage or crimp operations known heretofore for needle-suture attachment have their own particular shortcomings. In particular, these operations are difficult to control to achieve desired attachment parameters. Any variation in the crimping dies, the needle size, the needle aperture, or the suture size will increase variability of the needle suture attachment. Particularly with the manufacture of controlled release sutures, it heretofore has been critical to form the surgical needle to precise dimensions, i.e., the diameter of the needle and the size of the drilled hole need to be manufactured within a strict tolerance to achieve acceptable attachment. Similarly, the suture end to be attached to the needle has to be constructed within similar tight tolerances to assure that the combined tolerances of the suture and needle, when crimped with the crimping die apparatus, result in a "pull-out" force within a narrowly defined range. These manufacturing demands result in increased manufacturing time and waste and, hence, increased cost to the manufacturer.

A further disadvantage of conventional crimping operations is the distortion of the needle and lost symmetry caused by the crimping action. This is undesirable because it may result in an unacceptable pull-out force or increased trauma to tissue when the non-symmetrical needle is drawn through the tissue. For example, one conventional crimping method requires that the back end of the needle be struck with two opposed dies. The needle is then rotated 90° and the dies are arranged to strike the needle a second time. In effect, the first strike changes a round hole into one of elliptical shape, i.e., having a major and a minor axis. The second strike further distorts the needle. Furthermore, such procedures increase handling during manufacture and the likelihood that unacceptable attachment will be achieved. Indeed, rotating the suture and needle before the attachment is complete is likely to dislodge the suture tip in whole or part prior to completion of the attachment, resulting in unacceptable attachment. Moreover, multiple opposing die hits may produce a distorted needle end which results in corresponding asymmetry of tissue apertures and trauma during use.

In addition to size effects, the surface smoothness of the suture and the needle aperture, and the presence of any lubricants applied to either the suture or the needle may affect the resulting pull-out values. The conventional method of crimping, as described, underscores many of these parametric inconsistencies and necessarily utilizes multiple hits to overcome these process variabilities.

Commonly assigned U.S. Pat. Nos. 5,046,350 to Proto et al. and 5,099,676 to Proto et al. disclose crimping or swaging die configurations for attaching surgical needles and sutures. The split ring die disclosed in U.S. Pat. No. 5,046,350 includes a relief zone defined between a pair of extensions. A needle positioned between a pair of the split ring dies is stricken by the extensions whereby the superfluous material caused by the swaging action collects within the relief zone. The novel configuration of the split ring die provides a more uniform swage while the needle retains its circular symmetry in the area of suture attachment.

U.S. Pat. No. 5,099,676 discloses a die featuring a novel clover leaf shape which is defined by a generally circular surface having a series of interconnected alternating individual convex and concave curved surfaces. The convex and concave surfaces permit needle material swaged during the crimping process to flow from the convex portions which perform the actual crimping action to the concave areas so as to collect within the concave portions. The clover leaf dies provide unique attachment of the suture components and also maintains the symmetry of the product.

Although the crimping dies disclosed in the Proto et al. '350 and '676 patents have proven to be extremely effective for their intended purposes, the present disclosure is directed to further improvements whereby surgical needles and sutures of various sizes and types may be attached to desired attachment parameters. In accordance with the method and apparatus of the present disclosure, attachment is achieved while retaining the symmetry of the needle. Only a single "hit" on the needle end is required to accomplish the attachment thus minimizing handling of the suture and needle and reducing process control requirements.

SUMMARY

Generally stated, the present disclosure is directed to an apparatus for attaching a surgical needle having an end portion with an elongated aperture defined therein and a suture having a generally elongated end portion to be positioned in the elongated aperture of the needle. The apparatus includes a pair of dies, each die defining a longitudinal axis and having an inner die surface. The inner die surface includes at least two raised swaging portions extending generally along the longitudinal axis and a generally recessed portion defined between adjacent swaging portions and extending substantially along the lengths thereof. The swaging portions each have an engaging surface defining a plane angularly oriented relative to a longitudinal bisecting plane of the dies. The recessed portion defines a relief zone such that when the end portion of the suture is positioned within the aperture of the needle end and the dies are positioned about the end portion of the needle with the at least two swaging portions of each die generally facing the outer surface of the needle, applying inward crimping force to the dies causes the engaging surfaces of the dies to produce inward crimping forces on opposed sides of the needle end portion to cause a reduction of the dimension of the elongated aperture of the needle to thereby attach the needle to the suture, wherein the recessed portion defined between the adjacent swaging portions receive and collect deformed material from the needle.

In one preferred embodiment, each die includes two swaging portions with a recessed portion therebetween. Preferably, the swaging portions of each die are symmetrically arranged about the longitudinal plane whereby a first swaging portion of each die has an engaging surface which is oriented at a positive angle of orientation with respect to the longitudinal plane and a second swaging portion of each die has an engaging surface which is oriented at a negative angle of orientation with respect to the longitudinal plane. The angles of orientation defined by the engaging surfaces of the first and second swaging portions of each die are substantially equal in magnitude ranging in value from about 30° to about 60°. The recessed portion disposed between the first and second swaging portions of each die is generally arcuately-shaped defining a radius of curvature which is substantially constant throughout its length.

Each die may also include a secondary recessed portion disposed between each of the first and second swaging portions and a die face of the die. In an approximated swaging position of the dies, adjacent secondary recessed portions of the approximated dies define secondary relief zones to also receive and collect material displaced by the swaging action. The secondary relief zones are substantially similar in cross-sectional dimension to the cross-sectional dimension of the relief zone defined by the recessed portion disposed between the first and second swaging portions of each die.

The die configuration advantageously permits a wide range of sutures of different sizes to be attached to a single diameter bore in the needle without causing any cracking or failure at the needle-suture attachment preferably can be utilized to form non-detachable needle-suture combinations (where separation of the suture is accomplished by cutting or the like). Alternatively, it is contemplated that the dies can be utilized to form detachable needle-suture combinations (i.e., where the suture may be readily separated from the needle by a predetermined force by the user).

The present disclosure is also directed to a method for attaching a suture to a needle with the subject dies. A needle-suture combination formed by the apparatus and method of the present disclosure is also disclosed.

BRIEF DESCRIPTION OF THE DRAWINGS

Various embodiment(s) of the present disclosure is/are described herein with reference to the drawings, wherein:

FIG. 2 is a perspective view of the swaging dies constructed in accordance with the principles of the present disclosure;

FIG. 3 is an axial plan view of the dies of FIG. 2 in an initial open position illustrating a needle end positioned between the dies;

FIG. 4 is a cross-sectional view of the dies taken along the lines 4—4 of FIG. 3;

FIG. 5 is an axial plan view of the dies in an approximated close position swaging the needle end;

DETAILED DESCRIPTION OF THE PREFERRED EMBODIMENTS

Figure 1:
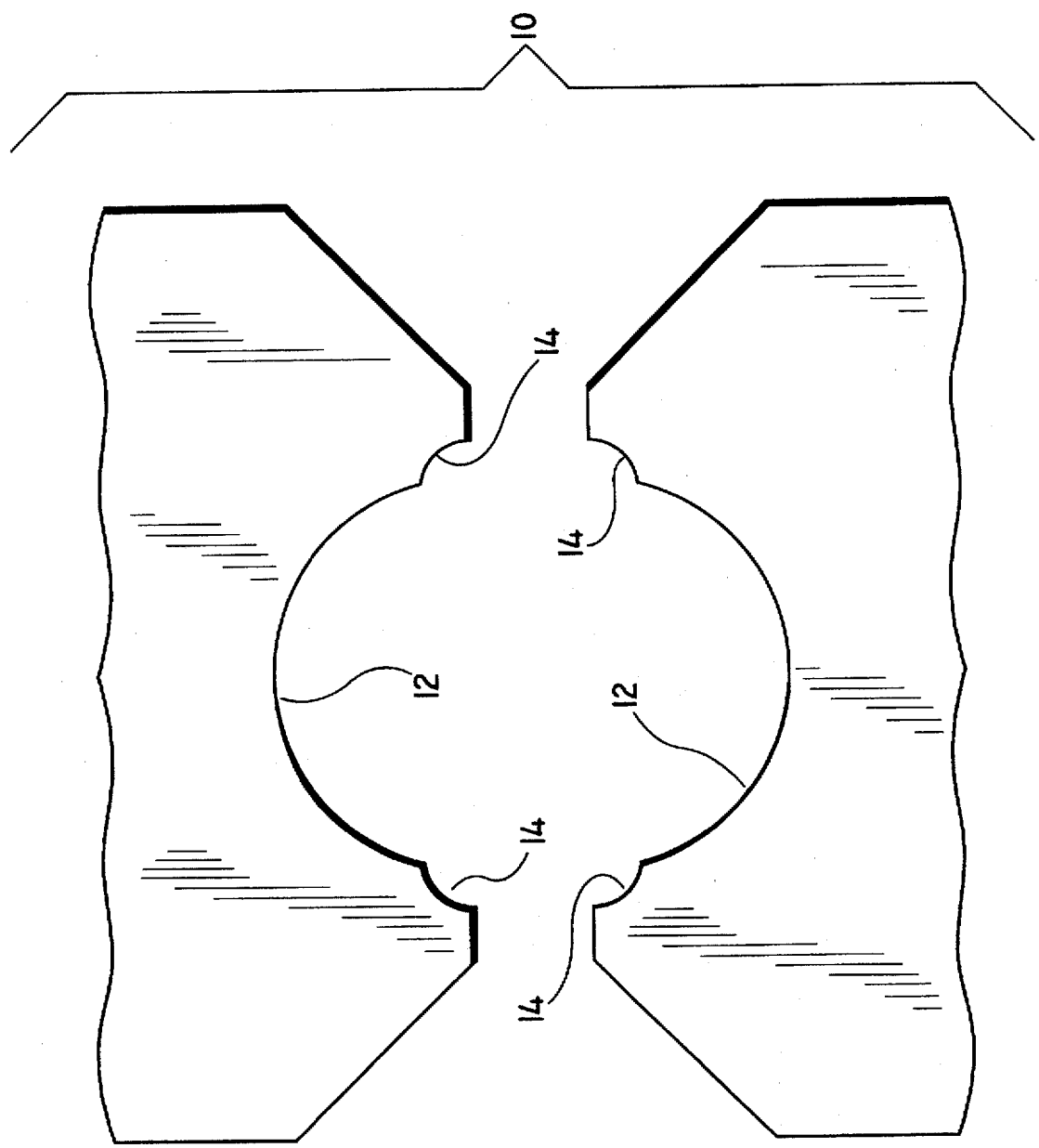
FIG. 1 is an axial plan view of a pair of conventional dual lap-overlap semicircular shaped dies.

Referring initially to FIG. 1, there is illustrated a pair of prior art dies 10 of a type utilized to attach a suture to a surgical needle. Each die 10 has a working surface at 12 of generally semi-circular shape and adjacent arcuate corner portions 14 to receive limited amounts of excess needle material overflowing during the crimping or swaging process. The arcuate corner portions 14 are of lesser radii than the working surface 12 and are not concentric therewith as shown.

To attach a needle to a suture, the dies 10 are positioned within an apparatus as will be described hereinbelow. The apparatus is arranged to cause both dies 10 to simultaneously move toward each other and strike a needle positioned between them. This causes the needle to become elliptical in cross-section and causes portions of the needle to deform into corner portions 14. Once the dies are impacted toward each other, they are separated and the needle is rotated 90°. The dies are then struck once again and the attachment is completed. In essence, the first strike causes the circular aperture in the needle to become elliptical. The second strike completes the attachment and reverses the distortion imparted to the needle. In certain instances, additional hits are required to positively secure the suture to the needle. This procedure necessitates at least a dual step attachment which in turn requires additional time and labor and results in loss symmetry of the needle end as stated above.

Referring now to FIGS. 2–4, there is illustrated a pair of dies constructed according to the principles of the present disclosure. Dies 20 are contemplated for use in attaching a needle of the type having a blunt end with a generally elongated aperture formed therein (i.e., a drilled needle) and a suture defining an end portion which is positioned within the elongated aperture of the needle. Dies 20 are advantageously configured to attach surgical sutures and needles of various sizes and types.

The particular arrangement of the dies 20 is best depicted in the axial view of FIG. 3 in which the dies 20 are shown with the blunt end portion of surgical needle 100 therebetween in a position to be attached to a suture 200 (shown in phantom) and in the cross-sectional view of FIG. 4 taken along lines 4—4 of FIG. 3. In FIGS. 2–4, the dies 20 are shown separated from each other in position prior to impact on a surgical needle 100. Surgical needle 100 has an aperture 110 where the end portion of suture 200 is positioned as best depicted in FIG. 4.

Dies 20 are identical in configuration with each die having a base 22 and a generally arcuate inner die surface 24. In an approximated position of dies 20, the inner die surfaces 24 of the dies 20 form an enclosure for reception of the drilled end portion (i.e., having aperture 110) of needle 100 during the swaging process. Each die 20 further defines an x-axis, a y-axis, and a z-axis as shown in FIG. 2.

Dies 20 each possess two raised swaging or crimping portions 26 equidistantly disposed relative to a central longitudinal bisecting plane, i.e., the "xz" plane of the die (FIG. 2), and interconnected by a centrally disposed concave surface or concavity 28. Each swaging portion 26 defines a primary planar swaging surface 30 which faces the needle 100. Surface 30 is preferably a planar surface and is oriented at an angle "a" (FIG. 3) ranging from about 30° to about 60° relative to both the "xz" plane of the die and the die face 32. In one preferred embodiment, swaging surface 30 is oriented at approximately a 45° angle relative to the "xz" plane and die face 32. For each die 20, the swaging surface 30 on one side of the "xz" plane defines a positive angle of orientation with respect to the "xz" plane while the swaging surface on the other side of the "xz" plane defines a negative angle of orientation with respect to the "xz" plane.

Swaging portion 26 also includes secondary swaging surfaces 34a, 34b disposed on each side of the primary swaging surface 30. The secondary swaging surfaces 34a, 34b are also preferably planar surfaces. As shown in FIG. 3, secondary swaging surface 34a of each die 20 preferably extends in a general transverse direction to the "xz" plane while secondary swaging surface 34b extends in general parallel relation to the "xz" plane. Other angular orientations of secondary swaging surfaces 34a, 34b are contemplated as well.

Each centrally disposed concavity 28 has a general arcuate configuration in cross-section preferably defining a radius which remains substantially constant throughout its length. Central concavity 28 extends along the entire longitudinal length or "z" axis of inner die surface 24 as best shown in FIGS. 2 and 4 and defines a material relief zone to receive needle material displaced by the dies 20 when the dies 20 are caused to strike the drilled needle end during the swaging process.

Each die 20 further includes secondary arcuate surfaces 36 disposed between each swaging portion 26 and die face 32, i.e., each secondary arcuate surface 36 extend from secondary swaging surface 34a of swaging portion 26 to the die face 32. In the approximated position of the pair of dies 20 shown in FIG. 5, adjacent secondary arcuate surfaces 36 define material relief zones which also receive needle material overflow caused by swaging action. The relief zones defined by the secondary arcuate surfaces 36 of the adjacent dies 20 are substantially similar in dimension to the relief zones defined by central arcuate surface 28.

Figure 6:
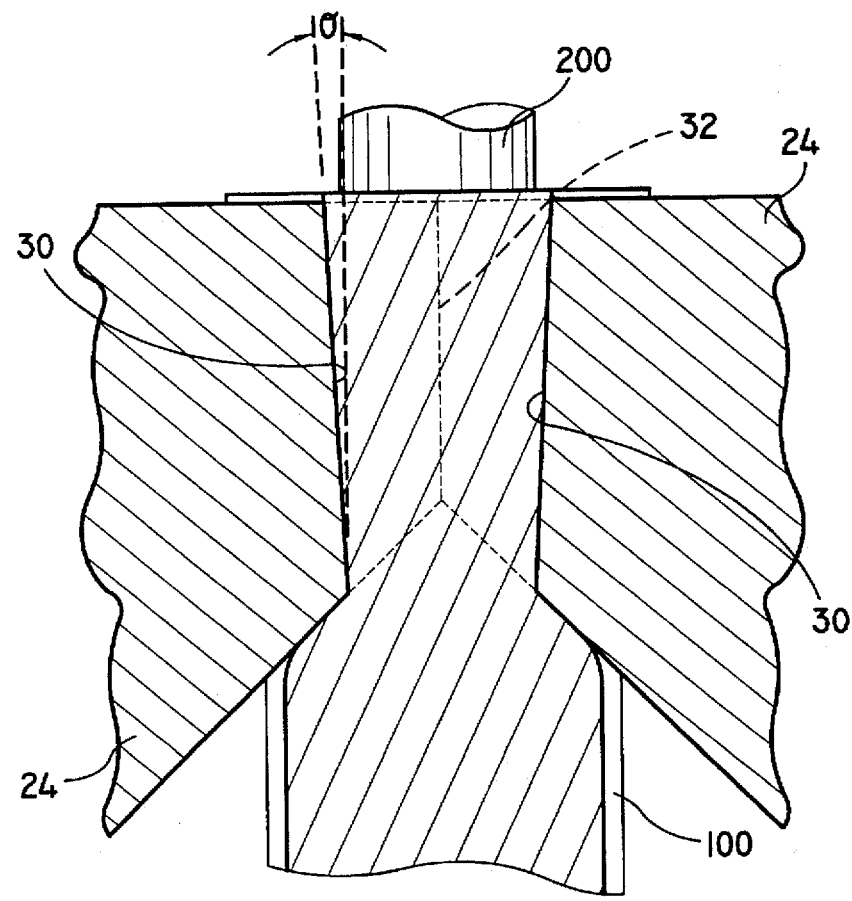
FIG. 6 is a cross-sectional view of the dies taken along the lines 6—6 of FIG. 5 illustrating the relative depth of the swage produced on the needle end.

Referring again to FIGS. 2–4, the inner surfaces 24 (i.e., including primary swaging surfaces 30, centrally disposed concave surfaces 28, second swaging surfaces 34a, 34b and secondary arcuate surfaces 36) taper outwardly from a front surface 38 of each die 20 to a rear surface 40 of the die 20 as shown in FIGS. 2 and 4. FIG. 3 illustrates this tapering configuration in phantom. FIG. 6 illustrates the taper angle θ defined between the swaging portions 26 of the dies and a plane parallel to die faces 32 and, hence, the longitudinal axis of the needle being swaged. Inner surface 24 tapers outwardly at an angle θ ranging from about 1° to about 7° relative to die face 32 and the "yz" plane (FIG. 2) of the die. In a preferred embodiment, this angle is about 2°.

Figure 7:
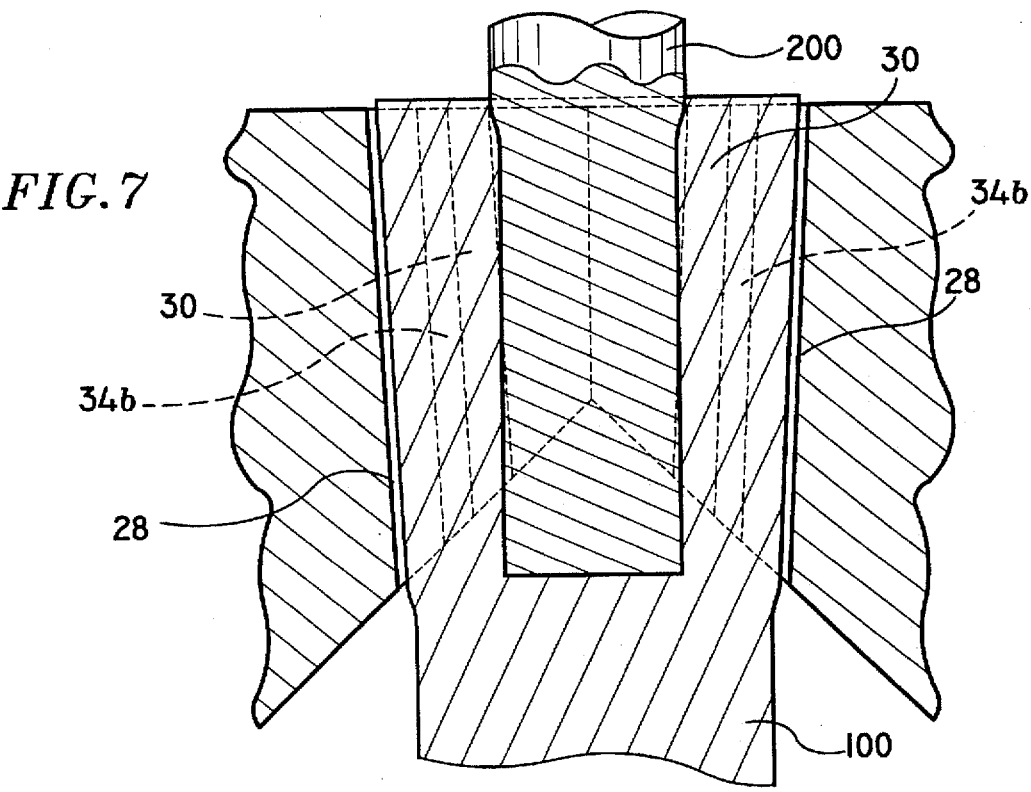
FIG. 7 is a cross-sectional view of the dies taken along the lines 7—7 of FIG. 5 illustrating the relief zones of the dies for accumulating needle material overflow displaced during the swaging.

FIGS. 5–7 illustrate the swaging effects dies 20 produce on the drilled needle end. During the swaging process, dies 20 are moved toward each other until die faces 32 of dies 20 meet whereby swaging portions 26 including primary swaging surfaces 30 and secondary swaging surfaces 34a, 34b strike the drilled end portion of needle 100.

FIG. 5 is an axial plan view of the dies, similar to the view of FIG. 3, but, illustrating the dies 20 in an approximated swaging position. As shown in FIG. 5, with die faces 32 contacting one another, the swaging portions 26 on each of the dies 20 are approximated to a predetermined position to appropriately symmetrically compress or swage the drilled needle end or needle attachment portion of needle 100 to secure the suture 200 within needle aperture 110. As shown, material overflow caused by swaging action is received within the relief zone defined by the central arcuate surfaces or concavities 28 as well as the relief zones defined by the adjacent secondary arcuate surfaces 36 of the approximated pair of dies 20. The result is a symmetrically configured swage on the needle 100 having four pairs of alternating concavities as produced by the swaging portions 26 and convexities as provided by the relief zones as shown in FIG. 5.

FIGS. 6–7 are cross sectional views taken along lines 6—6 and 7—7, respectively, of FIG. 5 and further illustrate the swaging effects on the needle end. FIG. 6 illustrates in cross-section the amount of radial inward movement of each die 20 and the swaging action of swaging portions 26 on the drilled needle end. The needle material which is engaged and displaced by the swaging portions 26 accumulate by the swaging action into the relief zones defined by the concave surfaces 28, 36. FIG. 7 illustrates the needle material displaced into central arcuate surface or concavity 28. Simultaneous, with the swaging action, the needle portion defining the aperture 110 of the needle will be effectively crimped and attached to the suture 200 by physical reduction of the dimension of the aperture 110 surrounding the suture.

Advantageously, the dies of the present disclosure require only one strike or "hit" to effect attachment of the suture components, thus, eliminating the double-hit method along with its inherent disadvantages. Preferably, dies 20 produce a non-detachable needle-suture combination, i.e., a "permanently" attached needle suture, however, it is contemplated that detachable needle-suture combinations also may be made with the dies 20. A further significant advantage of the present dies 20 resides in the fact that they advantageously allow a wide range of sutures to be used with a single diameter bore hole in the needle without causing any cracking or other failure of the needle at the drilled needle end due to the swaging. This appears to be attributed to the 1) unique capturing of the needle entirely within the dies 20 during swaging; 2) the symmetrical and radial compression of the needle end at least four equidistantly spaced peripheral locations (corresponding to the four swaging portions 26) to uniformly attach the needle to the suture; and 3) the sufficient depth of the crimp as provided by the elevated or raised swaging portions 26.

Figure 8:
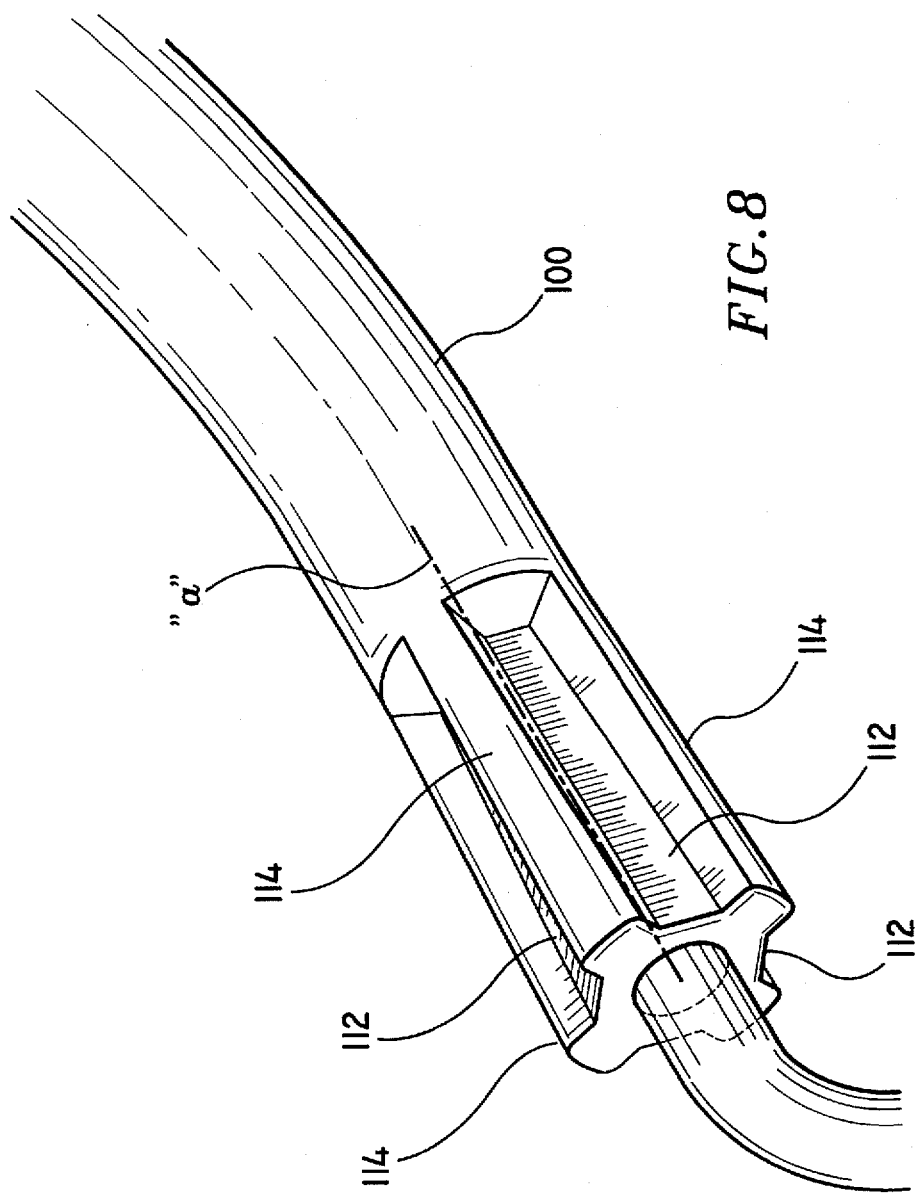
FIG. 8 is a perspective view of the needle end with attached suture as provided with the dies of the present disclosure.

Referring now to FIG. 8, the configuration of the needle 100 subsequent to attachment by dies 20 to suture 200 is illustrated. The primary swaging surfaces 30 of the dies 20 produce four equidistantly spaced planar surfaces 112 on the drilled end of the needle 100. As shown, the planar surfaces 112 are oriented at an angle relative to the longitudinal axis "a" of the needle as provided through the tapering orientation of the inner surfaces 24 of the dies 20. The planar surfaces 112 taper at an angle ranging from about 1° to about 7° preferably, about 2° as discussed above. The four equidistantly spaced arcuate raised portions 114 present on the needle end reflects the relief zones defined by central concave surfaces 28 and secondary arcuate surfaces 36 of the dies 20 where the material overflow is received during swaging. As shown, needle-suture attachment is achieved while maintaining the general symmetry of the needle with relatively insignificant surface distortion except for the minor impression formed on the surface. Thus, the needle 100 retains its generally circular symmetry in the area of suture attachment which thereby minimizes tissue trauma during the suturing process.

Figure 9:
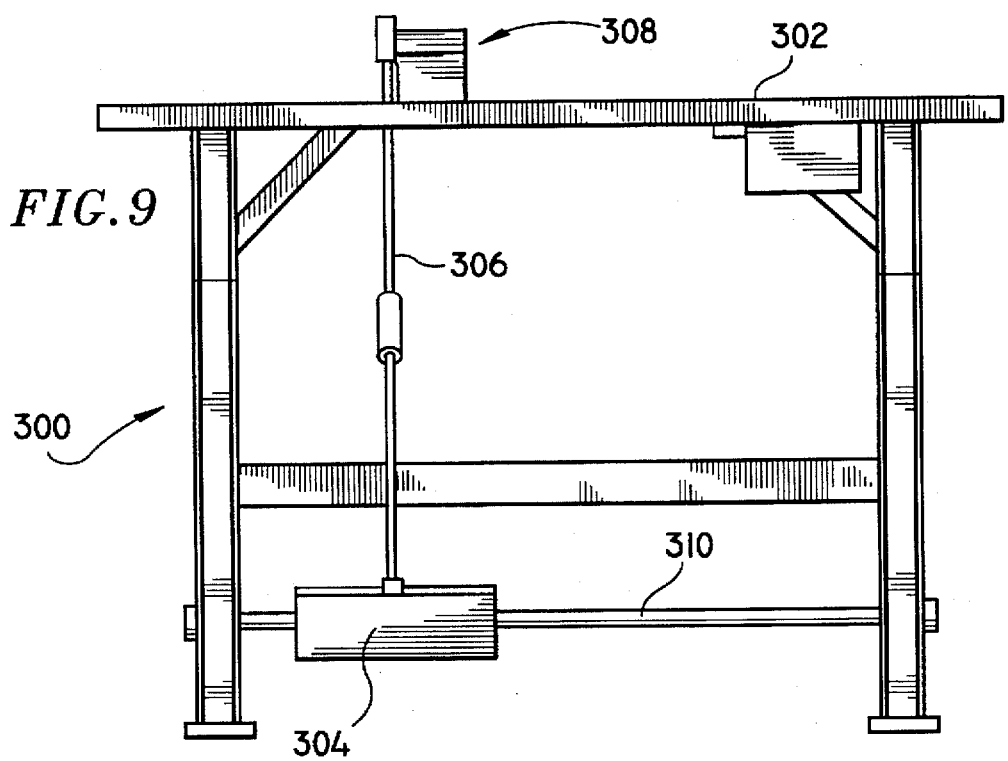
FIG. 9 is a front view of an apparatus with which the dies constructed according to the present disclosure may be utilized to attach a suture to a needle by crimping.
Figure 10:
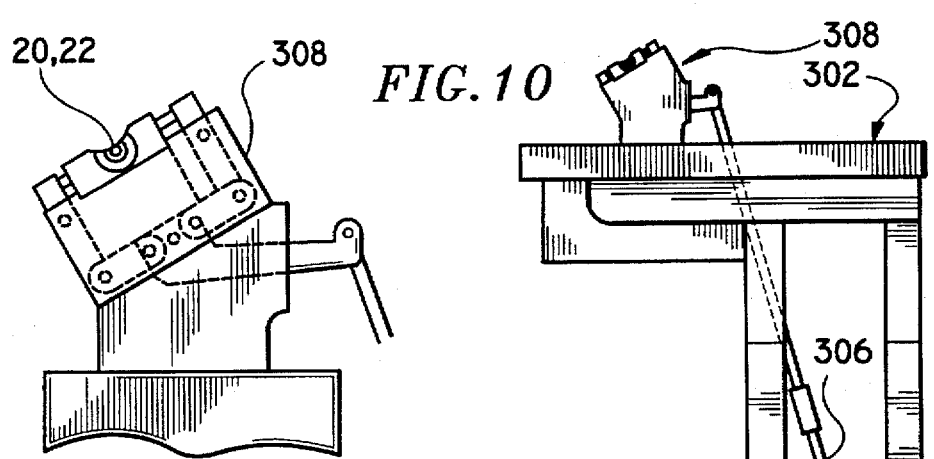
FIG. 10 is a side view of the apparatus shown in FIG. 9.

Referring now to FIGS. 9 and 10 there is shown an exemplary apparatus 300 on which sutures may be attached to needles utilizing the pair of dies 20 of the present disclosure. The apparatus 300 shown is manufactured and marketed as model 6A Suture Attaching Machine by B. G. Sulzel, Inc., Syracuse, N.Y. Other comparable machines suitable for attaching sutures may be utilized with the dies of the present disclosure.

The suture attaching machine 300 as illustrated in FIG. 9 includes a table 302 having treadle 304 which is foot operated and connected via treadle rod 306 to suture press 308. The treadle 304 is mounted for pivotal movement on pivot rod 310.

Figure 11:
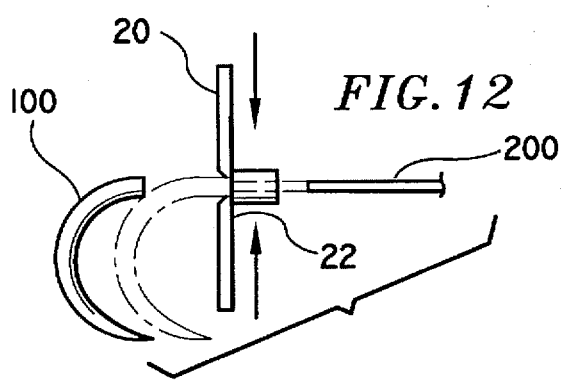
FIG. 11 is an enlarged view illustrating the dies of the present disclosure mounted in the apparatus of FIG. 9 for attaching a suture to a needle.

Referring now to FIG. 11, there is shown an enlarged side view of the suture press 308. As can be seen in FIG. 11, the pair of dies 20 which are constructed according to the disclosure are positioned within the jaws of the suture press 308 and arranged to be stricken against a needle 100 with the suture 200 in position as shown in FIG. 12.

Figure 12:
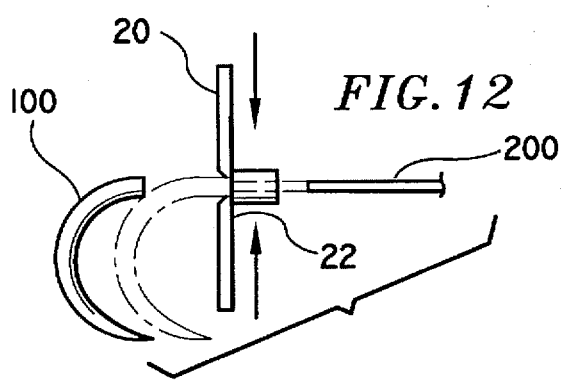
FIG. 12 is an enlarged side view of a pair of dies constructed according to the present disclosure positioned to attach a suture to a curved surgical needle.

The needle 100 shown in FIG. 12 is of a curved type having a straight rear end portion which defines an elongated aperture 110 dimensioned for reception and attachment to an appropriately sized suture 200. The needle 100 is supported on a guide support having a "V shaped" guide channel which positively determines and positions the needle location and orientation as shown. Thereafter, appropriate adjustments are made to predetermine the strike force to be transmitted to the needle and suture as may be appropriately calculated to obtain a predetermined pull-out force. The treadle is depressed to cause the dies to strike the needle.

An alternative apparatus for attaching surgical sutures to needles is disclosed in commonly assigned U.S. Pat. No. 5,350,373, which issued on Sep. 27, 1994, the contents of which are incorporated herein by reference. This apparatus includes a frame for positioning and maintaining the needle while the suture is being attached and a die system which selectively impacts the needle to secure the needle thereto. The die system may be modified to incorporate the novel dies 20 of the present disclosure.

It will be readily appreciated that the dies 20 of the present disclosure are particularly advantageous in that many types of sutures may be readily attached to needles having an aperture in their blunt end, i.e., drilled end needles. Further, single strike force is utilized thereby avoiding the need to provide "double-hit" attachment as necessary with prior art dies. This procedure provides a surgical needle-suture combination having a needle which is substantially symmetrical. Moreover, the single-hit attachment procedure provides consistent and controlled attachment of the suture and the needle which additionally reduces the time and effort to complete the attachment. Die life is increased, rejected needle/suture attachments are reduced, and attachment time is reduced. As a result, the cost of producing a surgical suture may be reduced.

The swaging dies 20 of the present disclosure may be utilized with all types of needles such as curved needles, straight needles, or the like, provided they have an elongated aperture on their end portion for receiving the suture. The elongated aperture preferably is a drilled hole, but also could be a channel formed in the end of the needle. Sutures usable with the present disclosure include silk, nylon, linen, cotton, polyester, polypropylene, stainless steel, natural materials such as catgut, synthetic polymers having glycolic acid ester linkages subject to hydrolytic degradation to non-toxic tissue compatible absorbable components, including polyglycolic acid. The sutures may be monofilamentary or braided, absorbable or non-absorbable. The dies of the present disclosure are preferably constructed of a hardened material such as tungsten carbide. However, it should be understood that all materials suitable for such die construction may be used, provided the geometric and configurational parameters taught by the present disclosure are met.

While the above description contains many specifics, these specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A surgical needle-suture attachment apparatus for attaching a surgical needle and a suture, which comprises a pair of dies, and a surgical needle having an end portion with an elongated aperture defined therein, each die defining a longitudinal axis and having an inner die surface, the inner die surface including at least two raised swaging portions extending generally along the longitudinal axis and a generally recessed portion defined between adjacent swaging portions and extending substantially along the lengths of adjacent swaging portions, the swaging portions each having an engaging surface defining a plane oriented at an acute angle relative to a longitudinal bisecting plane which bisects each die, the recessed portion defining a relief zone such that when an end portion of the suture is positioned within the aperture of the needle end and the dies are positioned about the end portion of the needle with the at least two swaging portions of each die generally facing the outer surface of the needle, applying inward crimping force to the dies causes the engaging surfaces of the dies to produce inward crimping forces on opposed sides of the needle end portion to cause a reduction of the dimension of the elongated aperture of the needle to thereby attach the needle to the suture, wherein the recessed portion defined between the adjacent swaging portions are for receiving and collecting deformed material from the needle.

2. The apparatus according to claim 1 wherein the swaging portions of each die are symmetrically arranged about the longitudinal bisecting plane.

3. The apparatus according to claim 2 wherein a plane defined by an engaging surface of a first swaging portion of each die is oriented at a positive angle of orientation with respect to the longitudinal bisecting plane and wherein a plane defined by an engaging surface of a second swaging portion of each die is oriented at a negative angle of orientation with respect to the longitudinal plane.

4. The apparatus according to claim 3 wherein the angles of orientation defined by the planes of the engaging surfaces of the first and second swaging portions of each die are substantially equal in magnitude.

5. The apparatus according to claim 4 wherein the angles of orientation defined by the planes of the engaging surfaces of the first and second swaging portions of each die range in magnitude from about 30° to about 60°.

6. The apparatus according to claim 3 including a secondary recessed portion disposed between each of the first and second swaging portions and a die face of each die, wherein in an approximated swaging position of the dies adjacent secondary recessed portions of the dies define secondary relief zones to receive and collect material displaced by the swaging action.

7. The apparatus according to claim 6 wherein the secondary relief zones are substantially similar in cross-sectional dimension to the cross-sectional dimension of the relief zone defined by the recessed portion disposed between the first and second swaging portions of each die.

8. The apparatus according to claim 1 wherein the recessed portion disposed between adjacent swaging portions of each die is generally arcuately-shaped.

9. The apparatus according to claim 8 wherein the recessed portion defines a radius of curvature which is substantially constant throughout its length.

10. An apparatus for attaching a first elongated member having an end portion with an elongated aperture defined therein and a second elongated member having a generally elongated end portion to be positioned in the elongated aperture of the first elongated member, which comprises a pair of dies, each die defining a longitudinal axis and having an inner die surface, the inner die surface including at least two raised swaging portions extending generally along the longitudinal axis and a generally recessed portion defined between adjacent swaging portions and extending substantially along the lengths of adjacent swaging portions, the swaging portions each having an engaging surface defining a plane oriented at an acute angle relative to a longitudinal bisecting plane and tapering outwardly from a front surface of the die to a rear surface of the die, the recessed portion defining a relief zone such that when an end portion of the second elongated member is positioned within the aperture of the first elongated member and the dies are positioned about the end portion of the first elongated member with the at least two swaging portions of each die generally facing the outer surface of the first elongated member, applying inward crimping force to the dies causes the engaging surfaces of the dies to produce inward crimping forces on opposed sides of the first elongated member portion to cause a reduction of the dimension of the elongated aperture of the first elongated member to thereby attach the first elongated member to the second elongated member, wherein the recessed portion defined between the adjacent swaging portions are for receiving and collecting deformed material from the first elongated member.

11. Apparatus for attaching a surgical needle and a suture, which comprises a pair of dies, and a surgical needle having an end portion with an elongated aperture defined therein, each die defining a longitudinal axis and having an inner die surface, the inner die surface having first and second generally longitudinally extending swaging surfaces with a recessed portion disposed between the swaging surfaces of each die, the swaging surfaces each defining a plane oriented at an acute angle relative to an intervening bisecting longitudinal plane disposed between the swaging surfaces of each die, the plane defined by the first swaging surface oriented at a positive angle of orientation with respect to the longitudinal intervening plane, the plane defined by the second swaging surface oriented at a negative angle of orientation with respect to the longitudinal intervening plane.

12. The apparatus according to claim 11 wherein the angles of orientation defined by the planes of the engaging surfaces of the first and second swaging portions of each die are substantially equivalent in magnitude.

13. The apparatus according to claim 12 wherein the recessed portion disposed between the swaging surfaces extends the entire lengths of the swaging surfaces.

14. A method for attaching a surgical needle to a suture, the needle having an end portion with an elongated aperture formed therein, the suture having an end portion suitably configured for insertion into the aperture, the method comprising the steps of:

positioning a pair of dies adjacent the needle end, each die defining a longitudinal axis and having an inner die surface portion, the inner die surface portion including at least two raised swaging portions extending generally along the longitudinal axis and a recessed portion disposed between adjacent swaging portions and extending the lengths thereof, the swaging portions of each die having an engaging surface defining a plane oriented at an acute angle relative to a longitudinal plane which is disposed between the swaging portions of each die, the engaging surfaces of the swaging portions facing the outer surface of the needle end and the recessed portion extending along the direction of the needle end which defines the elongated aperture;

inserting the suture end portion into the elongated aperture; and applying inward impact force to the dies to displace the dies toward each other causing the two engaging surfaces of each die to engage the outer surface of the needle end to thereby cause crimping of the needle end and reduction of an average dimension of the aperture defined therein, whereby the recessed portion disposed between the engaging surfaces is configured and dimensioned to permit deformed material of the needle to be received and collected therewithin so as to facilitate attachment of the needle and the suture.

15. The method according to claim 14 wherein the step of positioning a pair of dies includes providing each die having swaging portions which are symmetrically arranged about the longitudinal plane of the respective die.

16. The method according to claim 15 wherein said step of positioning a pair of dies comprises positioning a pair of dies wherein each die has an inner die surface portion having at least two raised swaging portions, a plane defined by a first swaging portion oriented at a positive angle with respect to the longitudinal plane of the die and a plane defined by a second swaging portion oriented at a negative angle of orientation with respect to the longitudinal plane of the die.

17. The method according to claim 16 wherein the angles defined by the planes of the engaging surfaces of each die are substantially equal in magnitude.

18. A method for attaching a surgical needle to a suture, the needle having an end portion with an elongated aperture formed therein, the suture having an end portion suitably configured for insertion into the aperture, the method comprising the steps of:

positioning a pair of dies adjacent the needle end, each die defining a longitudinal axis and having an inner die surface portion, the inner die surface portion including at least first and second raised swaging portions extending generally along the longitudinal axis and a recessed portion disposed between adjacent swaging portions and extending the lengths thereof, the first and second swaging portions of each die having respective first and second engaging surfaces, the first engaging surface defining a plane oriented at a positive acute angle relative to a longitudinal bisecting plane of the die, the second engaging surface defining a plane oriented at a negative acute angle relative to a longitudinal bisecting plane of the die, the angles defined by the planes of the first and second swaging portions range from about 30° to about 60°, the engaging surfaces of the swaging portions facing the outer surface of the needle end and the recessed portion extending along the direction of the needle end which defines the elongated aperture;

inserting the suture end portion into the elongated aperture; and applying inward impact force to the dies to displace the dies toward each other causing the two engaging surface of each die to engage the outer surface of the needle end to thereby cause crimping of the needle end and reduction of an average dimension of the aperture defined therein, whereby the recessed portion disposed between the engaging surfaces is configured and dimensioned to permit deformed material of the needle to be received and collected therewithin so as to facilitate attachment of the needle and the suture.

19. A needle-suture combination, which comprises:
a) a surgical needle including a sharp end and a blunt end, the blunt end defining an elongated aperture therein, the blunt end defining a longitudinal bisecting plane;
b) a suture having a generally elongated end portion which is positioned within the elongated aperture of the needle; and
c) a portion of the blunt end swaged to cause attachment of the needle to the suture, the swaged portion including at least two generally longitudinal extending planar surface portions and at least one substantially arcuate raised portion disposed between adjacent planar surface portions and extending substantially the lengths thereof, a first of the planar surface portions being disposed on one side of the longitudinal bisecting plane and being oriented at a positive acute angle of orientation with respect to the longitudinal bisecting plane and a second planar surface portion being disposed on the other side of the longitudinal bisecting plane and being oriented at a negative acute angle of orientation with respect to the longitudinal bisecting plane, at least one of the first and second planar surface portions also tapering toward the pointed end of the needle.

20. The needle-suture combination according to claim 19 wherein the planar surface portions are angularly offset relative to the longitudinal axis of the blunt end of a needle.

21. The needle-suture combination according to claim 19 wherein the swaged portion includes first and second pairs of opposed generally planar surface portions, each pair of planar surface portions having one substantially arcuate raised portion disposed between the planar surface portions of the pair, the arcuate raised portion extending substantially the lengths of the planar surface portions.

22. The needle-suture combination according to claim 21 including arcuate raised portions disposed between the first and second pairs of the planar surface portions.

23. The needle-suture combination according to claim 22 wherein the cross-sectional dimensions of the arcuate raised portions disposed between the first and second pairs of the planar surface portions are each substantially similar in dimension to the cross-sectional dimension of the arcuate-raised portion disposed between the planar surface portions of each pair.

24. The needle-suture combination according to claim 19 wherein the swaged portion includes four planar surface portions.

25. A needle-suture combination, which comprises:
a) a surgical needle including a pointed end and a blunt end, the blunt end having an elongated aperture therein and defining a longitudinal bisecting plane;
b) a suture having a generally elongated end portion which is positioned within the elongated aperture of the needle; and
c) a portion of the blunt end swaged to cause attachment of the needle to the suture, the swaged portion including first and second pairs of opposed generally longitudinal extending planar portions, each pair of planar portions having a first planar portion on one side of the longitudinal plane and being oriented at a positive acute angle of orientation with respect to the longitudinal plane and a second planar portion on the other side of the longitudinal plane and being oriented at a negative acute angle of orientation with respect to the longitudinal plane, the first planar portions of the first and second pairs of planar portions being in different planes and tapering toward the pointed end of the needle.

26. The needle-suture combination of claim 25 wherein the angles of orientation defined by the planes of the first and second planar portions of each die are substantially equal in magnitude.

27. The needle suture combination of claim 26 wherein the swaged portion includes a substantially arcuate raised portion disposed between the first and second planar portions of each pair of planar portions.

* * * * *